United States Patent
Liu (10) Patent No.: US 9,749,558 B2
(45) Date of Patent: Aug. 29, 2017

(54) SYSTEM AND METHOD FOR UTILIZING X-RAY DETECTOR HAVING PIXEL WITH MULTIPLE CHARGE-STORAGE DEVICES

(71) Applicant: GENERAL ELECTRIC COMPANY, Schenectady, NY (US)

(72) Inventor: James Zhengshe Liu, Salt Lake City, UT (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 14/741,739

(22) Filed: Jun. 17, 2015

(65) Prior Publication Data

US 2016/0373672 A1    Dec. 22, 2016

(51) Int. Cl.
| | |
|---|---|
| *G01T 1/24* | (2006.01) |
| *H04N 5/357* | (2011.01) |
| *G01T 1/208* | (2006.01) |
| *H04N 5/32* | (2006.01) |
| *G01N 23/04* | (2006.01) |

(52) U.S. Cl.
CPC .......... *H04N 5/3575* (2013.01); *G01T 1/208* (2013.01); *G01T 1/247* (2013.01); *H04N 5/32* (2013.01); *G01N 23/04* (2013.01); *G01N 2223/505* (2013.01)

(58) Field of Classification Search
USPC ....................................... 378/98.8
See application file for complete search history.

(56) References Cited

U.S. PATENT DOCUMENTS

| | | |
|---|---|---|
| 4,558,508 A | 12/1985 | Kinney et al. |
| 5,179,038 A | 1/1993 | Kinney et al. |
| 5,406,513 A | 4/1995 | Canaris et al. |
| 5,759,901 A | 6/1998 | Loh et al. |
| 6,583,470 B1 | 6/2003 | Maki et al. |
| 6,849,904 B2 | 2/2005 | Tien et al. |
| 7,498,584 B2 * | 3/2009 | Moody ............. H01L 27/14609 250/370.09 |
| 8,426,828 B2 | 4/2013 | Diericks |
| 9,658,347 B2 * | 5/2017 | Jacob ........................ H04N 5/32 |
| 2004/0211983 A1 | 10/2004 | Tien et al. |
| 2012/0002089 A1 * | 1/2012 | Wang ................ H01L 27/14603 348/297 |

(Continued)

*Primary Examiner* — Phillip A Johnston
(74) *Attorney, Agent, or Firm* — Fletcher Yoder, P.C.

(57) ABSTRACT

A digital X-ray imaging system is provided. The digital X-ray imaging system includes an X-ray source and a digital X-ray detector. The digital X-ray detector includes a scintillator configured to absorb radiation emitted from the X-ray source and to emit optical photons in response to the absorbed radiation. The digital X-ray detector also includes multiple pixels, each pixel including a pinned photodiode and at least two charge-storage capacitors coupled to the pinned photodiode, wherein each pixel is configured to absorb the optical photons emitted by the scintillator and each pinned photodiode is configured to generate a photocharge in response to the absorbed optical photons. The digital X-ray detector further includes control circuitry coupled to each pixel of the multiple pixels and configured to selectively control a respective flow of the photocharge generated by the pinned photodiode to a respective charge-storage capacitor of the at least two charge-storage capacitors during integration.

20 Claims, 6 Drawing Sheets

(56) References Cited

U.S. PATENT DOCUMENTS

| | | |
|---|---|---|
| 2013/0170615 A1 | 7/2013 | Wei et al. |
| 2014/0070361 A1 | 3/2014 | Benaissa et al. |
| 2014/0227859 A1 | 8/2014 | Benaissa et al. |
| 2015/0103973 A1 | 4/2015 | Liu et al. |

* cited by examiner

SYSTEM AND METHOD FOR UTILIZING X-RAY DETECTOR HAVING PIXEL WITH MULTIPLE CHARGE-STORAGE DEVICES

BACKGROUND

The subject matter disclosed herein relates to X-ray imaging systems, and more specifically, to X-ray imaging systems utilizing a digital X-ray detector having pixels with multiple charge-storage devices.

Digital X-ray imaging systems are becoming increasingly widespread for producing digital data which can be reconstructed into useful radiographic images. In current digital X-ray imaging systems, radiation from a source is directed toward a subject, typically a patient in a medical diagnostic application. A portion of the radiation passes through the patient and impacts a detector. The scintillator of the detector converts the radiation to light photons that are sensed. The detector is divided into a matrix of discrete picture elements or pixels, and encodes output signals based upon the quantity or intensity of the radiation impacting each pixel region, as measured by a receptor. The signals may then be processed to generate an image that may be displayed for review.

It may be desirable in digital X-ray imaging systems, e.g., utilizing certain types of detectors such as complementary metal-oxide-semiconductor (CMOS) detectors, to reduce electronic noise associated with low dose X-ray imaging applications. However, the ability to reduce electronic noise at low dose X-ray imaging applications may be limited by the structure of the pixel. Therefore, it may be desired to improve upon the pixel structure of the detectors to reduce electronic noise.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the present disclosure. Indeed, the present disclosure may encompass a variety of forms that may be similar to or different from the embodiments set forth below.

In accordance with a first embodiment, a digital X-ray imaging system is provided. The digital X-ray system includes an X-ray source. The digital X-ray imaging system also includes a digital X-ray detector that includes a scintillator configured to absorb radiation emitted from the X-ray source and to emit optical photons in response to the absorbed radiation. The digital X-ray detector also includes multiple pixels, each pixel including a pinned photodiode and at least two charge-storage capacitors coupled to the pinned photodiode, wherein each pixel is configured to absorb the optical photons emitted by the scintillator and each pinned photodiode is configured to generate a photocharge in response to the absorbed optical photons. The digital X-ray detector further includes control circuitry coupled to each pixel of the multiple pixels and configured to selectively control a respective flow of the photocharge generated by the pinned photodiode to a respective charge-storage capacitor of the at least two charge-storage capacitors during integration.

In accordance with a second embodiment, an X-ray imaging method is provided. The method includes on a digital X-ray system having a digital X-ray detector including a scintillator configured to absorb radiation emitted from an X-ray source and to emit optical photons in response to the absorbed radiation, multiple pixels, each pixel including a pinned photodiode and at least two charge-storage capacitors coupled to the pinned photodiode, performing the following steps. The steps include during resetting a capacitance of each pixel of the multiple pixels, storing a first reset noise in a first charge-storage capacitor of the at least two charge-storage capacitors and a second reset noise in a second charge-storage capacitor of the at least two charge-storage capacitors for each pixel. The steps also include during integration, generating a photocharge in each pinned photodiode and selectively diverting, via control circuitry, the photocharge to the respective first charge-storage capacitor for storage in each pixel of the multiple pixels based on a radiation dose of the radiation emitted. The steps further include sampling, via readout circuitry, the second reset noise from the respective second charge-storage capacitor in each pixel of the multiple pixels. The steps still further include sampling, via the readout circuitry, a signal representative of the photocharge stored in the respective first charge-storage capacitor in each pixel of the multiple pixels. The steps yet further include removing, via the readout circuitry, reset noise from the respective signal based on the respective second reset noise for each pixel of the multiple pixels to generate a respective noise-corrected signal. The steps even further include generating an exposure image based on the respective noise-corrected signals acquired from the multiple pixels.

In accordance with a third embodiment, an X-ray imaging method is provided. The method includes on a digital X-ray imaging system having a digital X-ray detector including a scintillator configured to absorb radiation emitted from an X-ray source and to emit optical photons in response to the absorbed radiation, multiple pixels, each pixel including a pinned photodiode, a first charge-storage capacitor coupled to the pinned photodiode, a second-charge storage capacitor coupled to the pinned photodiode, a first transfer gate coupled to the first charge-storage capacitor, and a second transfer gate coupled to the second charge-storage capacitor, performing the following steps. The steps include controlling the first and second transfer gates of each respective pixel of the multiple pixels, via control signals from control circuitry coupled to each pixel of the multiple pixels, in synchrony with radiation source pulse signals to divert, during a first integration, a first photocharge generated by each respective photodiode corresponding to radiation emitted at a first energy to each respective first charge-storage capacitor and to divert, during a second integration, a second photocharge generated by each respective photodiode derived from radiation emitted at a second energy to each respective second charge-storage capacitor, and the first energy is different from the second energy. The steps also include sequentially sampling, via readout circuitry, a first signal representative of the first photocharge stored in the respective first charge-storage capacitor and a second signal representative of the second photocharge stored in the respective second charge-storage capacitor in each pixel of the multiple pixels. The steps further include generating one or more X-ray images based on the first and second signals acquired from the multiple pixels.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

One or more specific embodiments of the present subject matter will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements.

The present disclosure provides for methods and systems to perform various X-ray imaging techniques utilizing a digital X-ray detector that includes discrete picture elements or pixels (e.g., multi-well pixels) that each has multiple charge-storage capacitors with each charge-storage capacitor coupled to a respective transfer gate. For example, the digital X-ray detector may be a complementary metal-oxide-semiconductor (CMOS) based detector. The multi-well pixels may be utilized in conjunction with the techniques described below to utilize correlated double sampling (e.g., dual-well pixels). The multi-well pixels may be utilized in conjunction with the techniques described below to reduce the electronic noise of the X-ray detector. The multi-well pixels may be utilized in conjunction with the techniques described below to reduce the time delay between X-ray pulses. The techniques described below may be utilized in a variety of radiographic imaging systems, such as computed tomography (CT) systems, fluoroscopic imaging systems, mammography systems, tomosynthesis imaging systems, conventional radiographic imaging systems, and so forth. However, it should be appreciated that the described techniques may also be used in non-medical contexts (such as security and screening systems and non-destructive detection systems).

Figure 1:
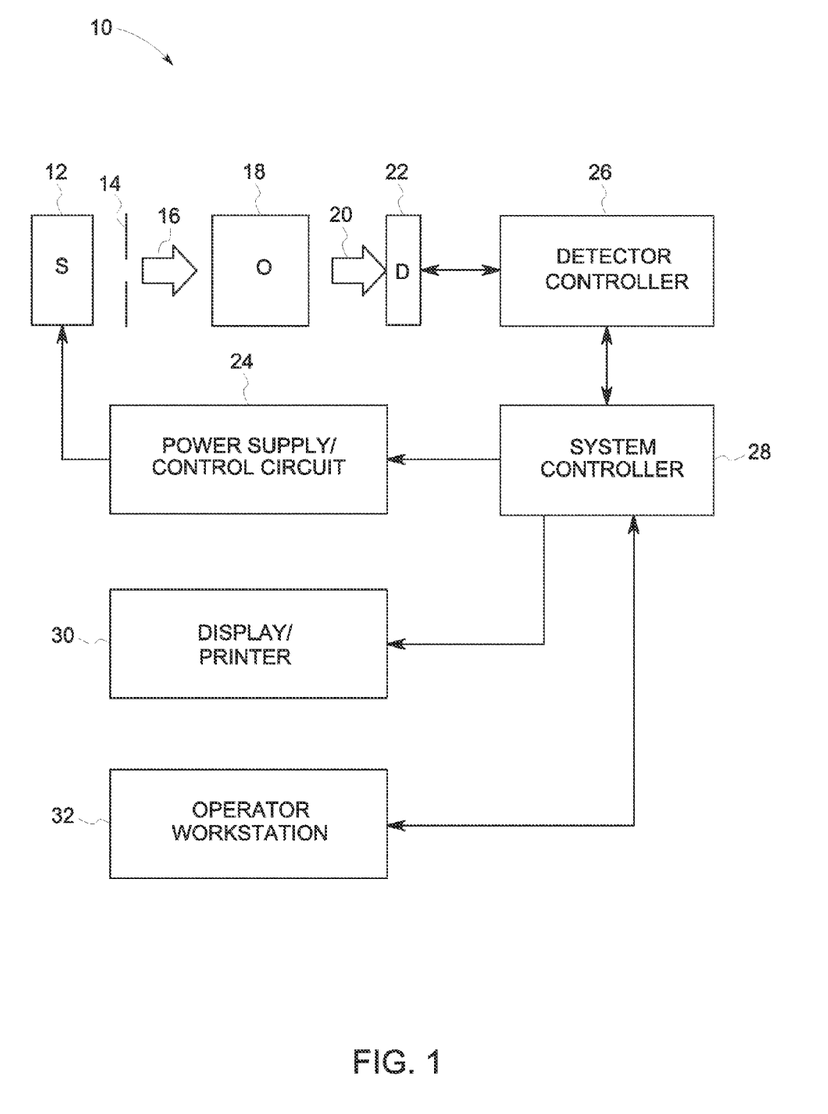
FIG. 1 is an embodiment of a digital X-ray system.

Turning now to the drawings, FIG. 1 illustrates diagrammatically an imaging system 10 for acquiring and processing discrete pixel image data. In the illustrated embodiment, system 10 is a digital X-ray system designed both to acquire original image data and to process the image data for display in accordance with the present technique. The imaging system 10 may be a stationary system disposed in a fixed X-ray imaging room or a mobile X-ray system. In the embodiment illustrated in FIG. 1, imaging system 10 includes a source of X-ray radiation 12 positioned adjacent to a collimator 14. Collimator 14 permits a stream of radiation 16 to pass into a region in which an object or subject is positioned. A portion of the radiation 20 passes through or around the subject and impacts a digital X-ray detector (e.g., CMOS detector), represented generally at reference numeral 22. The detector 22 may be portable or permanently mounted to the system 10. In certain embodiments, the detector 22 may convert the X-ray photons incident on its surface to lower energy photons, and subsequently to electric signals, which are acquired and processed to reconstruct an image of the features within the object or subject. In other embodiments, such as in a direct conversion implementation, the incident radiation itself may be measured without an intermediary conversion process.

Source 12 is controlled by a power supply/control circuit 24 which furnishes both power and control signals for examination sequences. Moreover, detector 22 includes a detector controller 26 (e.g., control circuitry) which commands acquisition of the signals generated in the detector 22. Detector controller 26 may also execute various signal processing and filtration functions, such as for initial adjustment of dynamic ranges, interleaving of digital image data, and so forth. Both power supply/control circuit 24 and detector controller 26 are responsive to signals from a system controller 28. In general, system controller 28 commands operation of the imaging system to execute examination protocols and to process acquired image data. In the present context, system controller 28 also includes signal processing circuitry and associated manufactures, such as optical memory devices, magnetic memory devices, or solid-state memory devices, for storing programs and routines executed by a processor to carry out various functionalities (e.g., determining which charge-storage capacitor of the multiple charge-storage capacitors of the multi-well pixel to utilize in storing the photocharge during integration based on the radiation dose of the imaging application, performing correlated double sampling, etc.), as well as for storing configuration parameters, thresholds (e.g., radiation dose threshold), and image data; interface protocols; and so forth. In one embodiment, a programmed computer system may be provided with hardware, circuitry, firmware, and/or software for performing the functions attributed to one or more of the power supply/control circuit 24, the detector controller 26, and/or the system controller 28 as discussed herein.

In the embodiment illustrated in FIG. 1, system controller 28 is linked to at least one output device, such as a display or printer as indicated at reference numeral 30. The output device may include standard or special purpose monitors and associated processing circuitry. One or more operator workstations 32 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
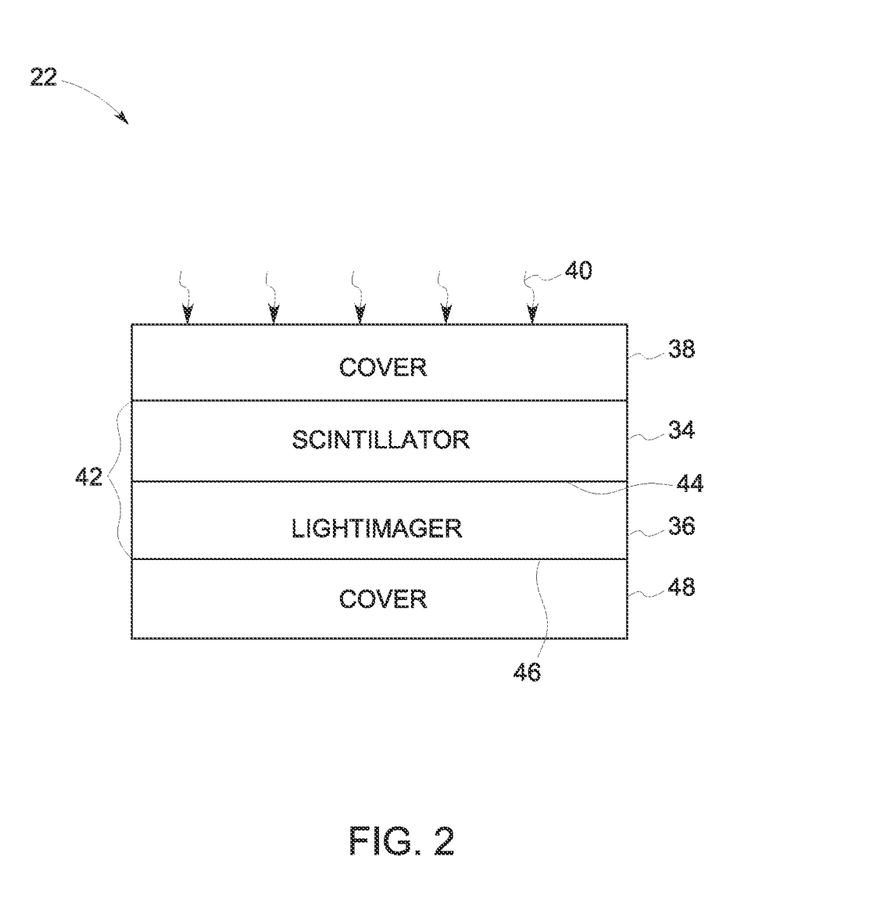
FIG. 2 is cross-sectional schematic view of an embodiment of a digital X-ray detector.

FIG. 2 is cross-sectional schematic view of an embodiment of a digital X-ray detector 22. The detector 22 includes a scintillator 34 that may be disposed directly on a light imager 36 (e.g., a CMOS light imager). Directly depositing the scintillator 34 on the light imager 36 may improve the detective quantum efficiency (DQE) of the detector. The components of the detector 22 illustrated may represent only some of the components present in such detection systems. For example, these detectors 22 may include electronics (e.g., including control circuitry, readout circuitry, etc.) and an outer cover 38, 48. As discussed herein, the digital X-ray detector 22 includes a detector array 42 that includes the scintillator 34 and the light imager 36 (e.g., a CMOS light imager). In addition, the light imager 36 includes a photosensitive area or pixel array. The scintillator may be fabricated from suitable scintillator compositions such as cesium iodide (CsI).

The light imager 36 includes a first surface 44 (e.g., the top surface) and a second surface 46 (e.g., the bottom surface) opposite from the first surface 44. The scintillator 34 is directly disposed on the first surface 44 of the light imager 36. The scintillator 34 converts X-ray photons 40 to light photons. The light imager 36 converts the light photons to electric signals for acquiring and processing image data. Generally, X-ray photons 40 are emitted from an X-ray radiation source 12, traverse the area in which an object or subject 18 is positioned, and collide with the scintillator 34 within the digital X-ray detector 22. The scintillator 34 absorbs the X-ray photons 40 and emits lower energy light photons that are proportional to the energy and amount of X-ray photons absorbed. As such, light emissions will be higher in those regions of the scintillator 34 where more X-ray photons were received. Since the composition of the object or subject 18 will attenuate the X-ray photons projected by the X-ray radiation source 12 to varying degrees, the energy level and amount of X-ray photons 40 colliding with the scintillator 34 will not be uniform across the scintillator 34. This non-uniformity results in a variation of light emission that will be used to generate contrast in a reconstructed image of the object or subject being imaged.

After the X-ray photons 40 are converted to light photons by the scintillator 34, the resulting light photons emitted by the scintillator 34 are detected by a photosensitive area in the light imager 36. The photosensitive area may include an array of photosensing elements or pixels to store an electric charge in proportion to the quantity of incident light absorbed by the respective photosensing elements. Generally, each photosensing element has a light sensing region and an electronically-controlled region for the storage and output of electric charge from that photosensing element. The light sensing region may be composed of a photodiode (e.g., pinned photodiode), which absorbs light and subsequently creates an electric charge for storage in one or more charge-storage capacitors. After an X-ray exposure, the electric charge in each pixel (e.g., one or more charge-storage capacitors) is read out (e.g., via readout circuitry) and processed by the digital X-ray imaging system 10.

As depicted in FIG. 2, the detector 22 includes an outer cover 38, 48 placed around the scintillator 34 and the light imager 36 to protect the detector array 42 from light contamination, environmental conditions (e.g., humidity), and/or to provide structural support. In an embodiment, the outer cover may include two separate pieces, a first cover 38 and a second cover 48 in a sandwich configuration for enclosing the scintillator 34 and the light imager 36 therebetween. The first cover 38 may be positioned on a top surface of the scintillator 34 and the second cover 48 may be positioned on a bottom surface of the light imager 36. In an embodiment, the first cover 38 and the second cover 48 may be a single piece that encloses the scintillator 34 and the light imager 36 therein. In certain embodiments, the first and second covers 38, 48 may be fabricated from carbon fiber, metal, metal alloy, plastic, a composite material or other suitable material.

In certain embodiments, light photons emitted from the scintillator 34 may travel towards the first cover 38 instead of the light imager 36. To redirect the light photons, the detector array 42 may include a light reflector, comprised of silver or other suitable light reflective material, disposed on a surface (e.g., a top surface) of the scintillator 34 opposite the light imager 36. The light reflector is designed to reflect light photons from the scintillator 34 back towards the light imager 36 resulting in less image noise, a stronger light signal, and more efficient overall performance of the digital X-ray detector 22.

In order to block moisture contamination, the digital X-ray detector 22 may include a moisture blocking layer and a sealing material. In certain embodiments, the moisture blocking layer or moisture blocking material (e.g., aluminum film) may be disposed between the outer cover 38, 48 and the detector array 42. In particular, a first moisture blocking layer may be disposed between the first cover 38 and the scintillator 34 or light reflector, and a second moisture blocking layer may be disposed between the light imager 36 and the second cover 48. In certain embodiments, a suitable waterproof sealing material may be disposed around the outer edges of the detector array 42 to seal the components of the detector array 42, including the scintillator 34, light imager 36, and a light reflector disposed on a surface (e.g., a top surface) of the scintillator 34.

Figure 3:
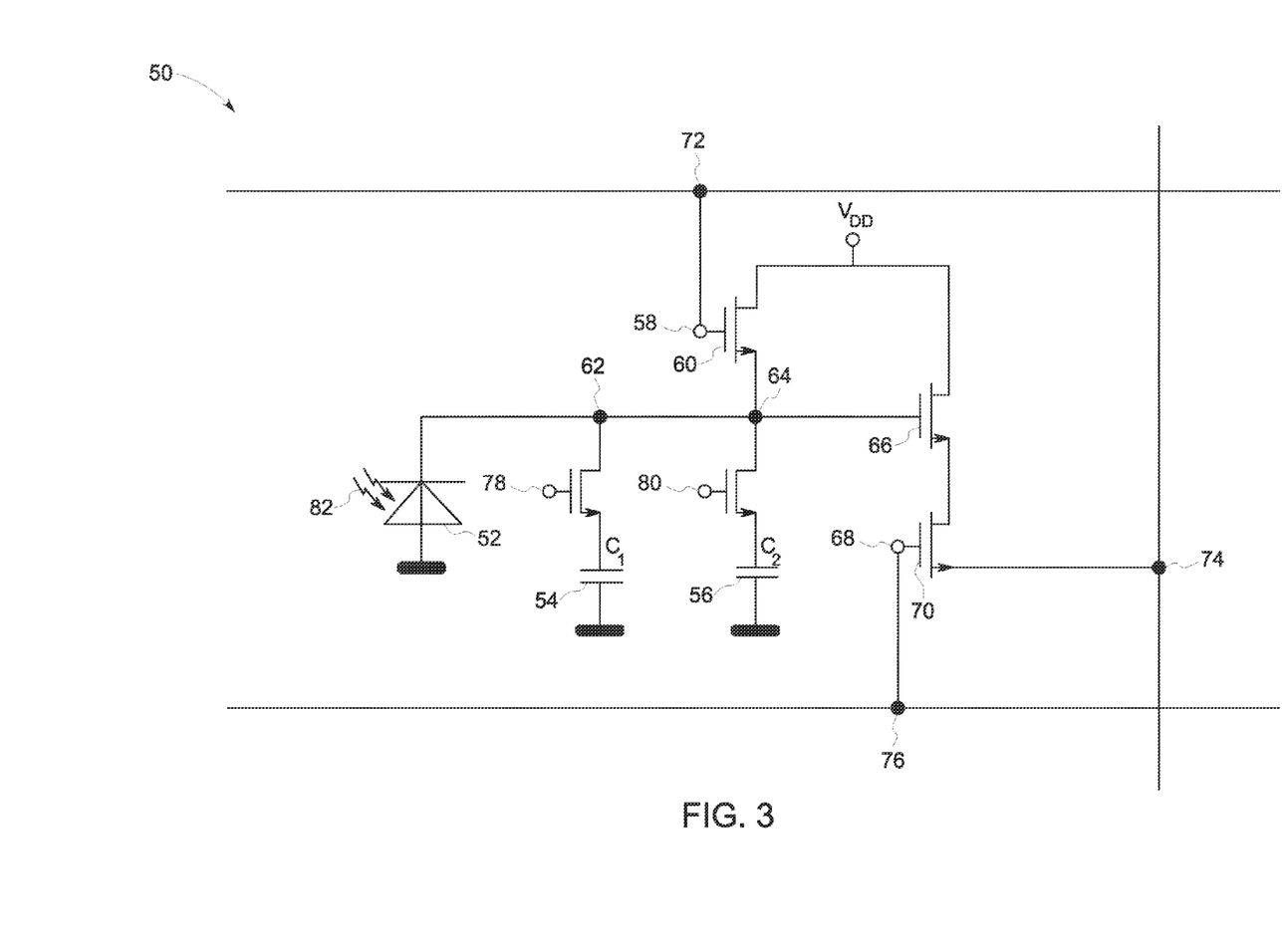
FIG. 3 is a schematic diagram of an embodiment of a multi-well pixel within a pixel array of a digital X-ray detector.

FIG. 3 is a schematic diagram of an embodiment of a multi-well pixel 50 (CMOS or crystalline silicon pixel) within a pixel array of the X-ray detector 22. The pixel 50, as depicted, is a dual-well pixel. The pixel 50 includes a photodiode 52 (e.g., pinned photodiode having p+ implants), a first charge-storage capacitor 54, a second charge-storage capacitor 56, a reset gate 58 on a reset transistor 60, a first charge amplifier gate 62 (associated with the first-charge storage capacitor 54) and a second charge amplifier gate 64 (associated with the second-charge storage capacitor 56) on a charge amplifier transistor 66, and a row select gate 68 on a row select transistor 70. In certain embodiments, the photodiode 52 is coupled to more than two charge-storage capacitors (e.g., 3, 4, 5, etc.). The first charge-storage capacitor 54 has a first capacitance, $C_1$, and the second charge-storage capacitor 56 has a second capacitance, $C_2$. In certain embodiments, $C_1$ and $C_2$ are different. In other embodiments, $C_1$ and $C_2$ are the same.

The cathode of the photodiode 52 is electrically coupled to the charge amplifier nodes 62, 64, which is electrically coupled to the source of the reset transistor 60 and the gate of the charge amplifier transistor 66. The anode of the photodiode 52 is electrically coupled to ground. The drains of the reset transistor 60 and the charge amplifier transistor 66 are electrically coupled to a supply voltage $V_{DD}$ (e.g., reference voltage). The source of the charge amplifier transistor 66 is electrically coupled to the drain of the row select transistor 70. The reset gate 58 is coupled to reset line 72 (e.g., part of the control circuitry). Common column data line 74 is coupled to the source of the row select transistor 70. The row select gate 68 is electrically coupled to row select scan line 76. The pixel 50 is accessed by the reset line 72, the common column data line 74, and the row select scan line 76. The electrical charge or photocharge generated by the photodiode 52 and stored in one of the capacitors 54, 56 is amplified by the charge amplifier transistor 66 (e.g., source follower) and fed on the common column data line 74 to be read out or sampled through the row select transistor 70. The purpose of the reset transistor 60 is to clear the electrical charge after it is read out or sampled.

The first charge-storage capacitor 54 is coupled to a first transfer gate 78 and the second charge-storage capacitor 56 is coupled to a second transfer gate 80. Both gates 78, 80 are coupled to control circuitry (not shown) to selectively connect or disconnect the capacitors 54, 56 to the other components of the pixel 50 and detector 22 (e.g., photodiode 52, reset circuitry, readout circuitry, etc.).

The depicted dual-well pixel 50 may be utilized in correlated double sampling. In the following discussion, as an example, $C_2$ is greater than $C_1$. In certain embodiments, $C_1$ is greater than $C_2$. The presence of the transfer gates 78, 80 enables the larger capacitor 56 to perform the function of a floating diffusion (FD) node when the smaller capacitor 54 is operating (i.e., being utilized during integration for storing photocharge generated by the photodiode 52) and the smaller capacitor 54 to perform the function of the FD node when the larger capacitor 56 is operating. Which capacitor 54, 56 may be utilized for the FD node and which capacitor 54, 56 may be utilized for integrating and storing the photocharge generated by the photodiode 52 may be determined by the detector 22 (e.g., control circuitry) based on the radiation dose of the imaging application or imaging sequence to be utilized with the detector 22. The detector 22 (e.g., control circuitry) may compare the radiation dose of the imaging application to a threshold (e.g., radiation dose threshold) to determine the respective function of the capacitors 54, 56. For example, if the expected radiation dose associated with the application is at or above the threshold (e.g., 20 rad/min), the smaller capacitor 54 may be utilized as the FD node and the larger capacitor 56 for integrating the generated photocharge. Conversely if the expected radiation dose associated with the application is below the threshold, the larger capacitor 56 may be utilized as the FD node and the smaller capacitor 54 for integrating the generated photocharge. Because of the supply voltage $V_{DD}$, photodiodes 52 (and their respective capacitors 54, 56) may be set to different potentials after reset (i.e., resetting capacitance of the pixels 50 (e.g., photodiodes and capacitors 54, 56). Correlated double sampling as described below accounts for these differences between the pixels 50.

Operation of the pixel 50 includes during the reset phase (i.e., resetting the capacitance of the pixel 50 and clearing any integrated charge), both gates 78, 80 are turned on (i.e., placed in a conducting state) via the control circuitry so that both capacitors are resetting at exactly the same moment. In such a way, the reset noise of capacitors 54 and 56 due to the fluctuation of the reference voltage, $V_{DD}$, will be correlated. The correlated reset noise (e.g., first reset noise in capacitor 54 and second reset noise in capacitor 56) are stored in both of the capacitors 54, 56. Reset noise in the two capacitors 54, 56 may not be equal to each other but correlated. Letting $n_1$ and $n_2$ be, respectively, the reset noise in electrons in the capacitors 54, 56 with capacitance $C_1$ and $C_2$ during a reset at which time the absolute temperature in the diode is T in Kelvin (K), provides the following:

$$n_1 = \frac{\sqrt{k_B T C_1}}{q_0}, \text{ and} \quad (1)$$

$$n_2 = \frac{\sqrt{k_B T C_2}}{q_0}, \quad (2)$$

where $q_0$ is the electrical charge of an electron and $k_B$ is the Boltzmann's constant. From equations (1) and (2), it is apparent that $$n_2 = \sqrt{\frac{c_2}{c_1}} \times n_1. \quad (3)$$

Thus, if the capacitance of one capacitor (e.g., capacitor 56) is four times the capacitance of the other (e.g., capacitor 54), the reset noise in that capacitor (e.g., capacitor 56) would be twice as much as that in the other capacitor (e.g., capacitor 54). The relationship between the reset noises can be accounted for by the readout circuitry that performs the correlated double sampling.

During exposure, operation of the pixel 50 includes X-ray photons 40 being converted into light photons 82 by the scintillator 34 and the light photons 82 being converted into electrons by the photodiode 52 to generate an electrical charge. If the radiation dose of the X-ray imaging application is at or above the radiation dose threshold, during integration, the control circuitry turns on the transfer gate 80 to enable the photocharge generated by the photodiode 52 to be diverted to capacitor 56 for storage, while transfer gate 78 for capacitor 54 is turned off (i.e., placed in a non-conducting state). After the exposure and integration, readout circuitry sequentially reads out the first reset noise from the capacitor 54 and the signal (i.e., stored photocharge) from the capacitor 56 (i.e., two correlated samplings) and removes reset noise from the signal based on the first reset noise. It should be noted that either the reset noise or the signal may be read first followed by the other. The capacitor 54, 56 being sampled has its respective transfer gate 78, 80 turned on during sampling, while the transfer gate 78, 80 of the other capacitor is turned off Utilizing correlated double sampling in the dual-well pixel 50 enables a reduction in electronic noise at a higher dynamic range.

If the radiation dose of the X-ray imaging application is below the radiation dose threshold, during integration, the control circuitry turns on the transfer gate 78 to enable the photocharge generated by the photodiode 52 to be diverted to capacitor 54 for storage, while transfer gate 80 for capacitor 54 is turned off (i.e., placed in a non-conducting state). After the exposure and integration, readout circuitry sequentially reads out the second reset noise from the capacitor 56 and the signal (i.e., stored photocharge) from the capacitor 54 (i.e., two correlated samplings) and removes reset noise from the signals based on the second reset noise.

In the alternative to correlated double sampling, the pixel 50 may also be utilized during X-ray imaging applications that utilize multiple energies (e.g., dual energy imaging applications having different peak kilovoltages (kVps) such as a low kVp and a high kVp). For example, during multi-energy X-ray imaging applications, the exposure sequence repeatedly alternates between two different energies or kVps (e.g., low kVp and high kVp) such as in a dual energy imaging application (e.g., to separate materials in the X-ray object). In embodiments where the pixel 50 is utilized during multi-energy X-ray applications, $C_1$ and $C_2$ of the respective capacitors 54, 56 may be different or the same.

During operation of the pixel 50, following the reset of capacitance of the pixel 50, the control circuitry in synchrony with X-ray tube or X-ray source signals, during integration, may turn on the transfer gate 78 of capacitor 54 and turn off the transfer gate 80 of the other capacitor 56 to enable the photocharge generated by the photodiode 52, in response to light photons derived from radiation at a first energy (e.g., low or high kVp), to selectively flow to the selected capacitor 54 for storage. Subsequently, during integration, the control circuitry may turn on the transfer gate 80 of capacitor 56 and turn off the transfer gate 78 of the other capacitor 54 to enable the photocharge generated by the photodiode 52, in response to light photons derived from radiation at a second energy (e.g., low or high kVp), to selectively flow to the selected capacitor 56 for storage. After integration, readout circuitry sequentially reads out the first signal (i.e., stored photocharge corresponding to the first energy) from the capacitor 54 and the second signal (i.e., stored photocharge corresponding to the second energy) from the capacitor 56 without an intervening reset of capacitance of the pixel 50 between read outs from the capacitors 54, 56. The capacitor 54, 56 being sampled has its respective transfer gate 78, 80 turned on during sampling, while the transfer gate 78, 80 of the other capacitor is turned off. Utilizing the dual-well pixel 50 in such a manner may reduce the time delay between the low and the high energy X-ray pulses. In particular, the dual-well pixel enables the acquisition of image data at multiple energies without having to read out the data between each different energy X-ray pulse during a sequence of pulses.

In certain embodiments, the pixel 50 may include one or more additional capacitors besides capacitors 54, 56. For example, in multi-energy imaging applications, for each additional charge-storage capacitor, an additional energy different from the first and second energies may be utilized during the exposure sequence.

Figure 4:
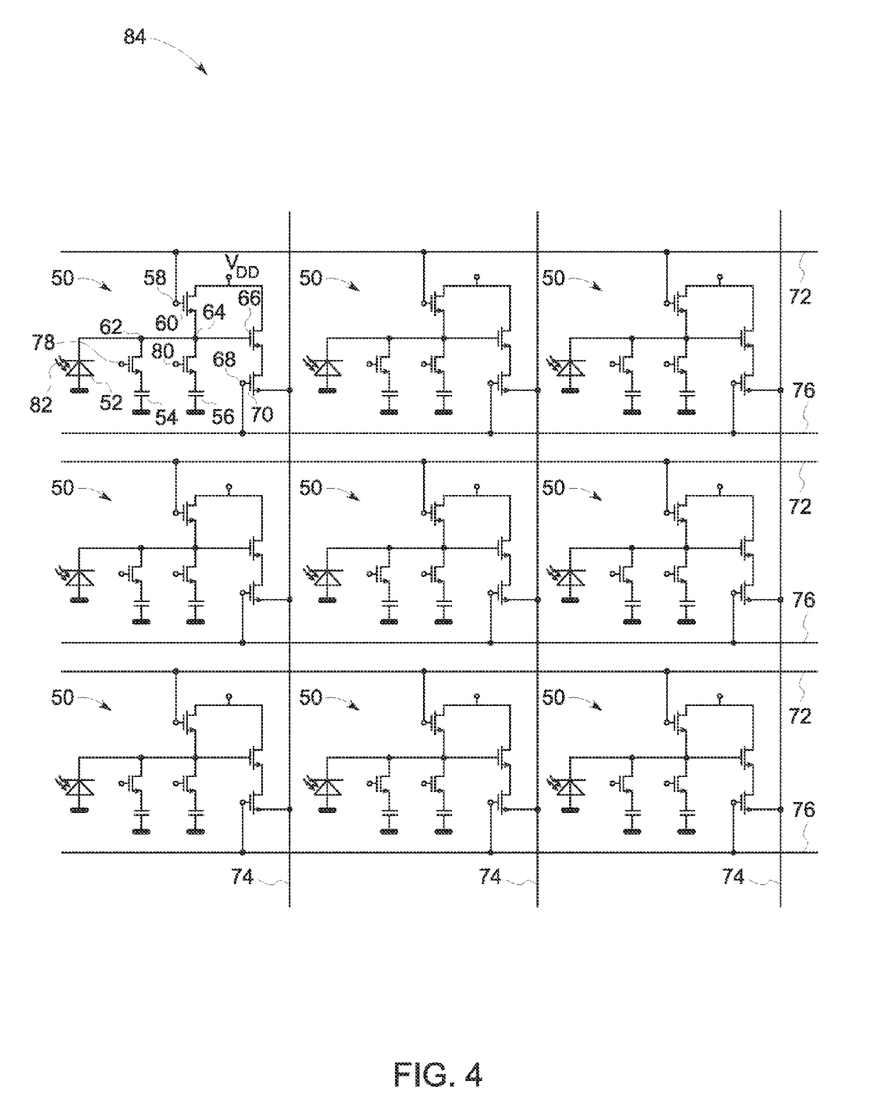
FIG. 4 is a schematic diagram of an embodiment of a two-dimensional (2D) pixel array within a digital X-ray detector.

FIG. 4 is a schematic diagram of an embodiment of a 2D pixel array 84 within the digital X-ray detector 22. The pixel array 84 includes an array of individual pixels 50 in an x-y grid allowing the pixels 50 to be accessed individually. Each pixel 50 is as described above in FIG. 3 (e.g., including at least two charge-storage capacitors 54, 56 coupled to respective transfer gates 78, 80). The accessibility of the individual pixels 50 in the pixel array 84 is achieved via the row select scan line 76 and the common column data line 74. The row select scan line 76 is used to address one row at a time, while the common column data line 74 is used to address one column at a time. The common column data line 74 sequentially addresses all of the columns during the period when their row is being addressed by the row select scan line 76. The common column data line 74 connects the output of all of the pixels 50 in the same column of the pixel array 84 through the row select gates 70. The row select gates 70 disconnect all pixels 50 except the selected pixel 50. The row select scan line 76 is used to select the desired row of pixels 50 to be read out. Similarly, the reset line 72 is used to reset all of the pixels 50 in a row.

Figure 5:
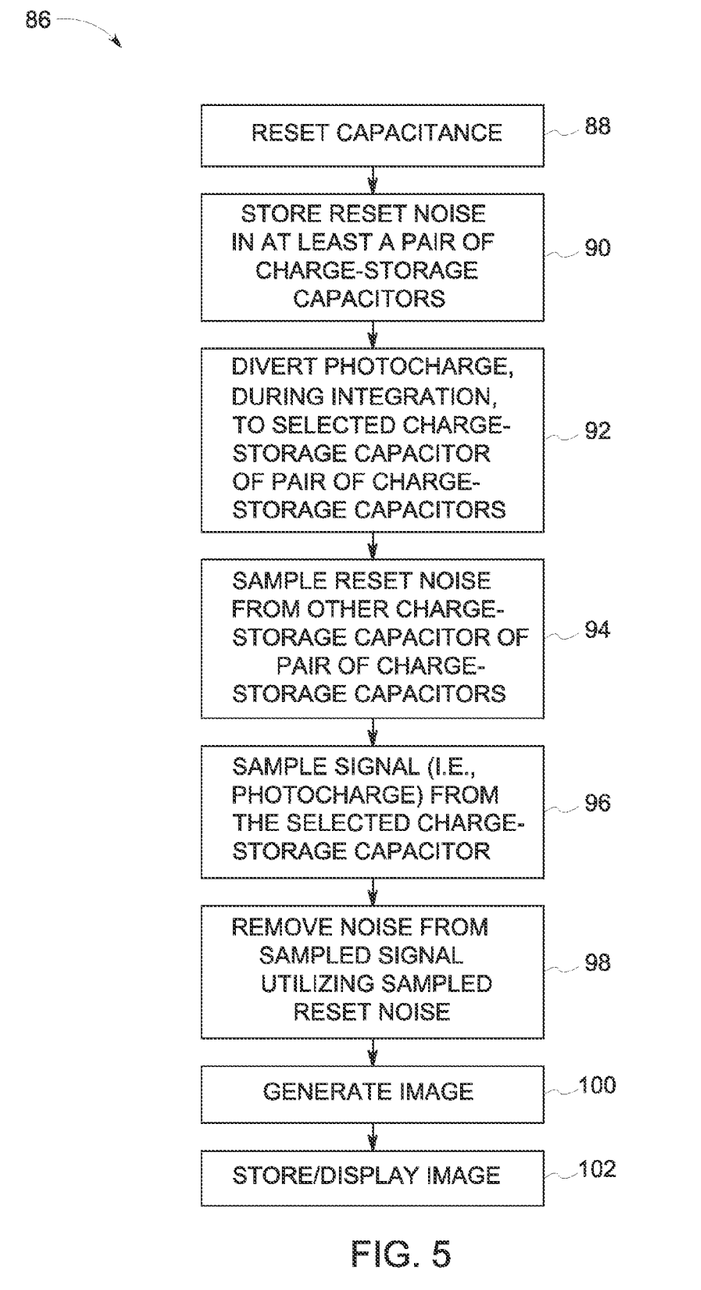
FIG. 5 is a flow chart of a method for acquiring image data utilizing a 2D pixel array of a digital X-ray detector (e.g., utilizing correlative double sampling)

FIG. 5 is a flow chart of a method 86 for acquiring image data utilizing a 2D pixel array 84 of the digital X-ray detector 22 (e.g., utilizing correlative double sampling). The pixel array 84 utilized in the method 86 is as described above in FIGS. 3 and 4. One or more of the following steps of the method 86 may be performed by one or more components of the imaging system 10 (e.g., detector 22, detector controller (e.g., control circuitry), readout circuitry, etc.). The pixels 50 utilized in the method 84 may include two or more charge storage-capacitors 54, 56. In the following discussion, as an example, $C_2$ is greater than $C_1$. In certain embodiments, $C_1$ is greater than $C_2$. The method 86 described in FIG. 5 may be utilized during a single X-ray exposure at a single energy or kVp. The method 86 includes resetting the capacitance of the pixels 50 (e.g., photodiode 52 and charge-storage capacitors 54, 56) as described above prior to an exposure and integration during the exposure (block 88) to clear any integrated charge within the pixels 50. As described above, the method 86 includes control circuitry turning on both transfer gates 78, 80 to enable correlated reset noise to be stored in both capacitors 54, 56 (block 90).

The method 86 also includes, during integration, diverting a photocharge generated via the photodiode 52 (via conversion of the received light photons) to a selected charge-storage capacitor of the pair of capacitors 54, 56 of each pixel 50 for storage (block 92). As described above, which capacitor 54, 56 may be utilized for the FD node and which capacitor 54, 56 may be utilized for integrating and storing the photocharge generated by the photodiode 52 may be determined by the detector 22 (e.g., control circuitry) based on the radiation dose of the imaging application or imaging sequence to be utilized with the detector 22. The detector 22 (e.g., control circuitry) may compare the radiation dose of the imaging application to a threshold (e.g., radiation dose threshold) to determine the respective function of the capacitors 54, 56. For example, if the radiation dose is at or above the threshold (e.g., 20 rad/min), the smaller capacitor 54 may be utilized as the FD node and the larger capacitor 56 for integrating the generated photocharge. If the radiation dose is below the threshold, the larger capacitor 56 may be utilized as the FD node and the smaller capacitor 54 for integrating the generated photocharge. The method 86 further includes sequentially sampling (e.g., via readout circuitry) reset noise from the other charge-storage capacitor not selected to store the photocharge during integration (block 94) and sampling the signal (i.e., stored photocharge) from the selected charge-storage capacitor (block 96). Steps 94 and 96 may be performed in any order. The method 86 still further includes removing reset noise from the sampled signal based on the sampled reset noise (block 98) via the readout circuitry. For example, if the reset noise was sampled from the capacitor 56 and the signal (i.e., stored charge) sampled from the capacitor 54, the readout circuitry removes the reset noise from the sampled signal from capacitor 54 based on the sampled reset noise from capacitor 56. The capacitor 54, 56 being sampled has its respective transfer gate 78, 80 turned on during sampling, while the transfer gate 78, 80 of the other capacitor is turned off. Conversely, if the reset noise was sampled from the capacitor 54 and the signal (i.e., stored charge) sampled from the capacitor 56, the readout circuitry removes the reset noise from the sampled signal from capacitor 56 based on the sampled reset noise from capacitor 54. An X-ray image (e.g., exposure image) may be generated from the reset noise-corrected image data acquired from the pixels 50 (block 100). The one or more generated images may be displayed (e.g., on display 30) or stored (e.g., on the imaging system or a hospital information system (HIS), a radiology information system (RIS), and/or picture archiving communication system (PACS)) (block 102). The multi-well pixels 50 may be utilized in conjunction with the technique described above to reduce the electronic noise of the CMOS based detector 22 (particularly during saturating levels of radiation).

Figure 6:
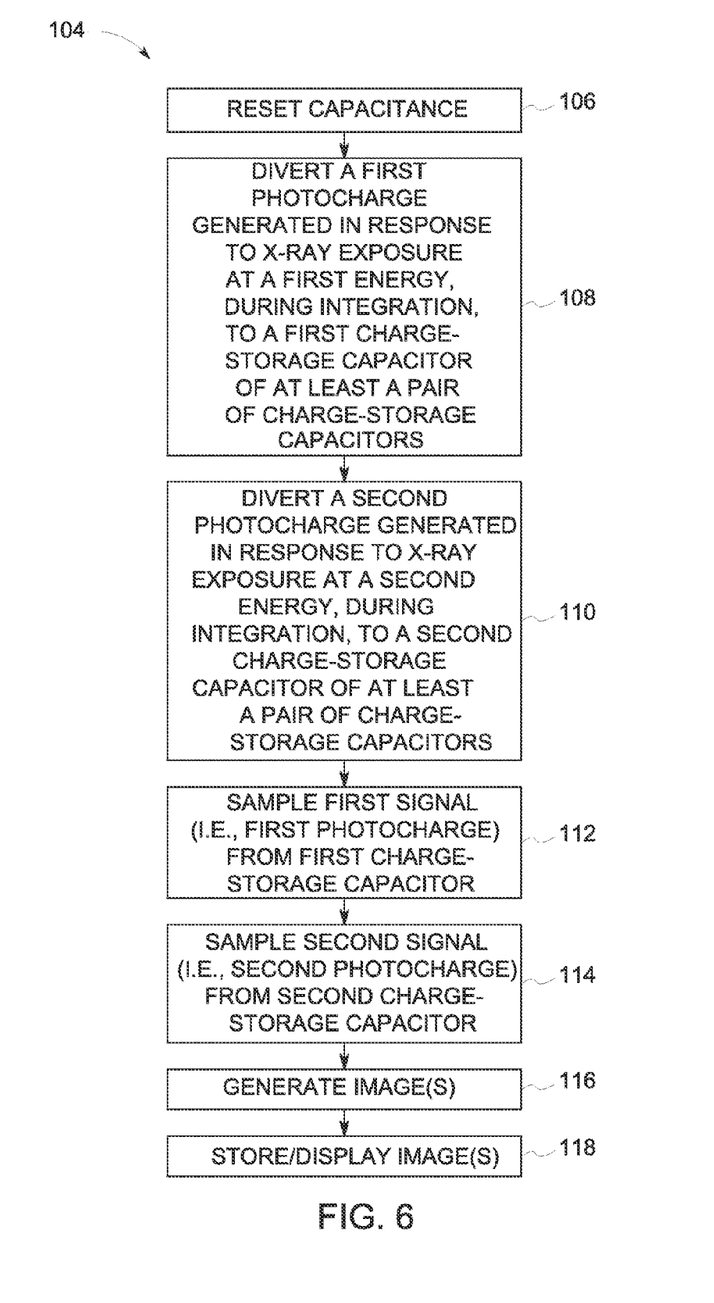
FIG. 6 is a flow chart of a method for acquiring image data utilizing a 2D pixel array of a digital X-ray detector (e.g., during a multi-energy X-ray imaging application).

FIG. 6 is a flow chart of a method 104 for acquiring image data utilizing the 2D pixel array 84 of the digital X-ray detector 22 (e.g., during a multi-energy X-ray imaging application). The pixel array 84 utilized in the method 104 is as described above in FIGS. 3 and 4. One or more of the following steps of the method 104 may be performed by one or more components of the imaging system 10 (e.g., detector 22, detector controller (e.g., control circuitry), readout circuitry, etc.). The pixels 50 utilized in the method 104 may include two or more charge storage-capacitors 54, 56. In the following discussion, $C_2$ and $C_1$ may be the same or different. The method 104 described in FIG. 6 may be utilized during a multi-energy exposure sequence repeatedly alternating between different energies or kVps (e.g., two (low kVp and high kVp). In certain embodiments, the method 104 may be utilized during a multi-energy exposure sequence repeatedly alternating between three or more different kVps. The method 104 includes resetting the capacitance of the pixels 50 (e.g., photodiode 52 and charge-storage capacitors 54, 56) as described above prior to a first sequence of a multi-energy X-ray exposure (e.g., low kVp X-ray pulse followed by a high kVp X-ray pulse) and integration during the exposure (block 106) to clear any integrated charge within the pixels 50. The method 104 includes, during a first integration, diverting a first photocharge generated via the photodiode 52 (via conversion of the received light photons corresponding to a first kVp or energy (e.g., low kVp, high kVp) to one of the capacitors 54, 56 for storage (block 108). Subsequent to step 108, the method 104 includes, during a second integration, diverting a second photocharge generated via the photodiode 52 (via conversion of the received light photons corresponding to a second kVp or energy (e.g., different from the first kVp) to the other capacitor 54, 56 for storage (block 110). As described above, steps 108 and 110 are carried out by the detector 22 via the control circuitry in synchrony with X-ray tube or X-ray source signals to selectively turn the transfer gates 78, 80 on and off as described above to selectively divert the photocharge to the selected capacitor 54, 56.

The method 104 further includes sequentially sampling (e.g., via readout circuitry) a first signal (i.e., first stored photocharge corresponding to the first energy) from the capacitor 54, 56 storing the first signal (block 112) and sampling the signal (i.e., second stored photocharge corresponding to the second energy) from the other capacitor 54, 56 (block 114). The capacitance of the pixels 50 is not reset in between these samplings in steps 112 and 114. As a result, the image data corresponding to the different energies may be sampled or acquired faster than in typical multi-energy capacitors utilizing typical pixels 50. The capacitor 54, 56 being sampled has its respective transfer gate 78, 80 turned on during sampling, while the transfer gate 78, 80 of the other capacitor is turned off.

Subsequent to reading out the image data from the pixels 50 for the multi-energy X-ray exposure sequence, the capacitance of the pixels 50 is reset prior to next sequence of X-ray pulses at different kVps (block 106). The method 104 also includes generating one or more images (e.g., low kVp image, high kVp image, images from both the low and high kVp image data such as a bone-only image and a tissue-only image, etc.) from the image data (block 116) sampled from the capacitors 54, 56. The one or more generated images may be displayed (e.g., on display 30) or stored (e.g., on the imaging system or a hospital information system (HIS), a radiology information system (RIS), and/or picture archiving communication system (PACS)) (block 118). The multi-well pixels 50 may be utilized in conjunction with the technique described above to increase the dynamic range and/or temporal resolution of the detector 22.

Technical effects of the disclosed embodiments include providing the x-ray detector 22 that includes multi-well pixels 50 that each include multiple charge-storage capacitors 54, 56 coupled to respective transfer gates 78, 80. The multi-well pixels 50 may be utilized in conjunction with the technique described above to reduce the electronic noise of the X-ray detector 22. In addition, the multi-well pixels 50 may be utilized in conjunction with the techniques described above to reduce the time delay between the low and the high energy X-ray pulses in dual-energy applications.

This written description uses examples to disclose the subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A digital X-ray imaging system comprising:
   an X-ray source; and
   an X-ray detector comprising:
     a scintillator configured to absorb radiation emitted from the X-ray source and to emit optical photons in response to the absorbed radiation;
     a plurality of pixels, each pixel comprising a pinned photodiode, at least two charge-storage capacitors coupled to the pinned photodiode, and the at least two charge-storage capacitors coupled to a charge amplifier transistor, wherein each pixel is configured to absorb the optical photons emitted by the scintillator and each pinned photodiode is configured to generate a photocharge in response to the absorbed optical photons to be directly diverted, during integration, to a respective charge-storage capacitor of the at least two charge-storage capacitors for storage; and
     control circuitry coupled to each pixel of the plurality of pixels and configured to selectively control a respective flow of the photocharge generated by the pinned photodiode to the respective charge-storage capacitor of the at least two charge-storage capacitors for storage during integration.

2. The digital X-ray imaging system of claim 1, wherein the at least two charge-storage capacitors in each pixel of the plurality of pixels comprise a first charge-storage capacitor and a second charge-storage capacitor, and each pixel of the plurality of pixels comprises a first transfer gate coupled to the first charge-storage capacitor and a second transfer gate coupled to the second charge-storage capacitor, and the control circuitry is configured to selectively control the flow of the photocharge generated by the pinned photodiode to the respective first and second charge-storage capacitors via control signals sent to the respective first and second transfer gates.

3. The digital X-ray imaging system of claim 2, wherein in each pixel of the plurality of pixels the first charge-storage capacitor has a first capacitance and the second charge-storage capacitor has a second capacitance, and the second capacitance is greater than the first capacitance.

4. The digital X-ray imaging system of claim 3, wherein the control circuitry is configured to turn on both the first and second transfer gates in each pixel of the plurality of pixels during reset of capacitance to enable storage of a first reset noise in the first charge-storage capacitor and a second reset noise in the second charge-storage capacitor.

5. The digital X-ray imaging system of claim 4, wherein the control circuitry is configured to determine for each pixel of the plurality of pixels which of the respective first and second charge-storage capacitors to divert the respective flow of the photocharge to during integration based on a radiation dose of the radiation emitted.

6. The digital X-ray imaging system of claim 5, wherein, if the radiation dose, is below a radiation dose threshold, the control circuitry is configured to turn on the first transfer gate and to turn off the second transfer gate of each pixel of the plurality of pixels to divert the respective flow of the photocharge during integration to the respective first charge-storage capacitor for storage.

7. The digital X-ray imaging system of claim 6, comprising readout circuitry configured to sample data from the pinned photodiode of each pixel of the plurality of pixels to perform correlated double sampling, wherein the readout circuitry is configured to sample the second reset noise from each respective second charge-storage capacitor, to sample a signal representative of the photocharge stored in the first charge-storage capacitor from each respective first charge-storage capacitor, and to remove reset noise from the respective signal based on the respective second reset noise.

8. The digital X-ray imaging system of claim 5, wherein, if the radiation dose, is at or above the radiation dose threshold, the control circuitry is configured turn off the first transfer gate and to turn on the second transfer gate of each pixel of the plurality of pixels to divert the respective flow of the photocharge during integration to the respective second-charge storage capacitor for storage.

9. The digital X-ray imaging system of claim 8, comprising readout circuitry configured to sample data from the pinned photodiode of each pixel of the plurality of pixels and to perform correlated double sampling, wherein the readout circuitry is configured to sample the first reset noise from each respective first charge-storage capacitor, to a sample a signal representative of the photocharge stored in the second charge-storage capacitor from each respective second charge-storage capacitor, and to remove reset noise from the respective signal based on the respective first reset noise.

10. The digital X-ray imaging system of claim 2, wherein the control circuitry is configured to selectively control the first and second transfer gates of each pixel via the control signals applied to respective first and second transfer gates in synchrony with X-ray source pulse signals received from a source controller coupled to the X-ray source.

11. The digital X-ray imaging system of claim 10, wherein the control circuitry is configured to selectively control the first and second transfer gates of each pixel via the control signals in synchrony with the X-ray source pulse signals to divert a first photocharge derived from radiation emitted at a first energy to the first charge-storage capacitor for storage during a first integration and to subsequently divert a second photocharge derived from radiation emitted at a second energy to the second charge-storage capacitor for storage during a second integration, and the first energy is different from the second energy.

12. The digital X-ray imaging system of claim 11, comprising readout circuitry configured to sample data from the pinned photodiode of each pixel of the plurality of pixels, wherein the readout circuitry is configured to sequentially sample a first signal representative of the first photocharge stored in the first charge-storage capacitor for each pixel and sample a second signal representative of the second photocharge stored in the second charge-storage capacitor for each respective pixel without resetting a capacitance of each respective pixel between sampling the first and second signals.

13. The digital X-ray imaging system of claim 1, wherein each pixel of the plurality of pixels comprises a complementary metal-oxide-semiconductor pixel or crystalline silicon pixel.

14. An X-ray imaging method, comprising:
on a digital X-ray imaging system having a digital X-ray detector comprising a scintillator configured to absorb radiation emitted from an X-ray source and to emit optical photons in response to the absorbed radiation, a plurality of pixels, each pixel comprising a pinned photodiode, at least two charge-storage capacitors coupled to the pinned photodiode, and the at least two charge-storage capacitors coupled to a charge amplifier transistor, performing the steps of:
during resetting a capacitance of each pixel of the plurality of pixels, storing a first reset noise in a first charge-storage capacitor of the at least two charge-storage capacitors and a second reset noise in a second charge-storage capacitor of the at least two charge-storage capacitors for each pixel;
during integration, generating a photocharge in each pinned photodiode and both selectively and directly diverting, via control circuitry, the photocharge to the respective first charge-storage capacitor for storage in each pixel of the plurality of pixels based on a radiation dose of the radiation emitted;
sampling, via readout circuitry, the second reset noise from the respective second charge-storage capacitor in each pixel of the plurality of pixels;
sampling, via the readout circuitry, a signal representative of the photocharge stored in the respective first charge-storage capacitor in each pixel of the plurality of pixels;
removing, via the readout circuitry, reset noise from the respective signal based on the respective second reset noise for each pixel of the plurality of pixels to generate a respective noise-corrected signal; and
generating an exposure image based on the respective noise-corrected signals acquired from the plurality of pixels.

15. The X-ray imaging method of claim 14, wherein each pixel of the plurality of pixels comprises a first transfer gate coupled to the first charge-storage capacitor and a second transfer gate coupled to the second charge-storage capacitor, and comprising, during resetting the capacitance of each pixel, turning on, via the control circuitry, both the first and second transfer gates in each pixel of the plurality of pixels for storing the first reset noise in the first charge-storage capacitor and the second reset noise in the second charge-storage capacitor.

16. The X-ray imaging method of claim 15, wherein selectively diverting, via the control circuitry, the photocharge to the respective first charge-storage capacitor for storage in each pixel of the plurality of pixels comprises turning on the first transfer gate and turning off the second transfer gate of each pixel of the plurality of pixels to divert the photocharge to the respective first charge-storage capacitor for storage.

17. The X-ray imaging method of claim 16, wherein the first charge storage capacitor has a first capacitance and the second charge-storage capacitor has a second capacitance, and the second capacitance is greater than the first capacitance.

18. The X-ray imaging method of claim 16, wherein the first charge storage capacitor has a first capacitance and the second charge-storage capacitor has a second capacitance, and the first capacitance is greater than the second capacitance.

19. An X-ray imaging method, comprising:
on a digital X-ray imaging system having a digital X-ray detector comprising a scintillator configured to absorb radiation emitted from an X-ray source and to emit optical photons in response to the absorbed radiation, a plurality of pixels, each pixel comprising a pinned photodiode, a first charge-storage capacitor coupled to the pinned photodiode, a second-charge storage capacitor coupled to the pinned photodiode, a first transfer gate coupled to the first charge-storage capacitor, a second transfer gate coupled to the second charge-storage capacitor, and the first and second charge-storage capacitors coupled to a charge amplifier transistor, performing the steps of:
controlling the first and second transfer gates of each respective pixel of the plurality of pixels, via control signals from control circuitry coupled to each pixel of the plurality of pixels, in synchrony with X-ray source pulse signals to directly divert, during a first integration, a first photocharge generated by each respective photodiode corresponding to radiation emitted at a first energy to each respective first charge-storage capacitor for storage and to directly divert, during a second integration, a second photocharge generated by each respective photodiode derived from radiation emitted at a second energy to each respective second charge-storage capacitor for storage, and the first energy is different from the second energy;
sequentially sampling, via readout circuitry, a first signal representative of the first photocharge stored in the respective first charge-storage capacitor and a second signal representative of the second photocharge stored in the respective second charge-storage capacitor in each pixel of the plurality of pixels;
generating one or more X-ray images based on the first and second signals acquired from the plurality of pixels.

20. The X-ray imaging method of claim 19, wherein sequentially sampling, via the readout circuitry, the first and second signals from each pixel of the plurality of pixels is performed without resetting a capacitance of each respective pixel between sampling the first and second signals.

* * * * *